(12) United States Patent
Wakamatsu

(10) Patent No.: US 8,601,859 B2
(45) Date of Patent: Dec. 10, 2013

(54) SENSING DEVICE

(75) Inventor: Shunichi Wakamatsu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 704 days.

(21) Appl. No.: 12/802,833

(22) Filed: Jun. 15, 2010

(65) Prior Publication Data
US 2010/0319438 A1 Dec. 23, 2010

(30) Foreign Application Priority Data

Jun. 22, 2009 (JP) .................................. 2009-147973

(51) Int. Cl.
G01N 29/02 (2006.01)
G01N 29/36 (2006.01)

(52) U.S. Cl.
USPC .................... 73/61.79; 73/61.49; 73/64.53

(58) Field of Classification Search
USPC ................... 73/61.45, 61.49, 61.79, 64.53
See application file for complete search history.

(56) References Cited

U.S. PATENT DOCUMENTS

| 7,036,375 B2 | 5/2006 | Nozaki |
| 2004/0187580 A1 | 9/2004 | Nozaki |

FOREIGN PATENT DOCUMENTS

| JP | 3-252563 | 11/1991 | |
| JP | 11-183479 | 7/1999 | |
| JP | 2002-148295 | 5/2002 | |
| JP | 2002-243608 | 8/2002 | |
| JP | 2002-277368 | 9/2002 | |
| JP | 2002-310872 | 10/2002 | |
| JP | 2004-317493 | 11/2004 | |
| JP | 2005-530177 | 10/2005 | |
| JP | 2005-315830 | 11/2005 | |
| JP | 2006-258787 | 9/2006 | |
| JP | 2006-266947 | 10/2006 | |
| JP | 2007-085973 | 4/2007 | |
| JP | 2007-108170 | 4/2007 | |
| WO | WO 2007/077963 | * | 7/2007 |
| WO | WO 2007/077967 | * | 7/2007 |
| WO | WO 2008/041733 | * | 4/2008 |
| WO | WO 2008050891 | * | 5/2008 |

* cited by examiner

Primary Examiner — Daniel S Larkin
(74) Attorney, Agent, or Firm — Jordan and Hamburg LLP

(57) ABSTRACT

To provide a sensing device capable of easily sensing a substance to be sensed with high accuracy. When sensing, by supplying a sample solution to an absorption layer 46 while oscillating a quartz-crystal resonator 4 to make the absorption layer absorb a substance to be sensed in the sample solution, the substance to be sensed based on an amount of variation in an oscillation frequency of the quartz-crystal resonator 4 after an absorption time elapses, the quartz-crystal resonator 4 is oscillated, before supplying the sample solution to the absorption layer 46, to measure the oscillation frequency of the quartz-crystal resonator 4 at a predetermined measurement interval, for instance, at every one second, and the oscillation frequency of the quartz-crystal resonator 4 is stabilized for the same period of time as a measuring time 19 until the measurement result becomes equal to or less than a frequency tolerance value 19b previously set based on a measurement sensitivity of the substance to be sensed.

5 Claims, 15 Drawing Sheets

| MEASUREMENT SENSITIVITY (Hz) | 5 | 10 | 10 | ----- | 100 |
|---|---|---|---|---|---|
| MEASUREMENT ERROR RANGE (Hz) | 0.5 | 1 | 1.5 | ----- | 10 |

SENSING DEVICE

BACKGROUND OF THE INVENTION

1. Field of the Invention

The present invention relates to a sensing device which senses, by making an adsorption layer formed on an electrode provided on a piezoelectric piece adsorb a substance to be sensed in a sample fluid, the substance to be sensed based on a variation in natural frequency of the piezoelectric piece.

2. Description of the Related Art

As a device for sensing a trace substance in a solution or gas, there has been known a sensing device which uses QCM (Quarts Crystal Microbalance) formed by a quartz-crystal resonator which is a piezoelectric resonator mainly formed by an AT-cut quartz-crystal piece as a piezoelectric piece. A sensing device of this type senses a presence/absence or a concentration of a trace substance in a sample fluid by making the aforementioned quartz-crystal resonator that forms a quartz-crystal oscillator circuit adsorb the trace substance and detecting a difference between an oscillation frequency (resonance frequency) after the absorption of the trace substance and an oscillation frequency before the absorption of the trace substance or an oscillation frequency of a quartz-crystal resonator for reference in which the trace substance is not absorbed. Examples of the trace substance are dioxin which is an environmental pollutant in the air, a specific antigen in blood or serum, and so on, and the sensing device senses an extremely low concentration, for example, on ppb to ppt level, of these substances.

Such a sensing device is structured by forming an excitation electrode for oscillating the aforementioned piezoelectric piece on a surface of the piezoelectric piece, for instance, and by further stacking an absorption layer such as, for instance, an antibody that absorbs a trace substance on the excitation electrode. Further, by making the absorption layer absorb the trace substance as described above to measure an oscillation frequency of a quartz-crystal resonator, a presence/absence or a concentration of the trace substance in a sample fluid is calculated based on, for example, a previously determined calibration curve or threshold value.

Incidentally, a piezoelectric piece requires a period of time from the start of its oscillation to the stabilization of the oscillation, and when being oscillated in a liquid phase, it particularly requires a long period of time until the oscillation is stabilized. Further, also when the piezoelectric piece in a state of oscillating in a vapor phase in a stabilized manner is put in a liquid phase, it requires a long period of time for stabilizing the oscillation. Therefore, when a trace substance is sensed, there is a need to provide a waiting time for waiting until an oscillation frequency of the piezoelectric piece is stabilized to a predetermined value, before supplying a sample fluid to an absorption layer, for instance, and then to start the sensing (measurement) of a substance to be sensed after the waiting time is elapsed. However, it is extremely difficult to judge whether the oscillation frequency is stabilized or not, and experience and judgment of an operator, for instance, are necessary for detecting the trace substance in a short period of time with high accuracy. Specifically, if the measurement is started before the oscillation frequency of the piezoelectric piece is stabilized, the detection accuracy of the trace substance is lowered, and if the waiting time which is longer than necessary is provided, the period of time required for the measurement is increased. Further, when the aforementioned sample fluid is a liquid, a liquid such as a buffer solution, for instance, is supplied to the piezoelectric piece before the measurement to stabilize the oscillation frequency, but, since the longer period of time is required in the liquid, than in the gas, until the oscillation frequency of the piezoelectric piece is stabilized, it is further difficult to find out whether the oscillation frequency of the piezoelectric piece is stabilized or not.

Although Patent Documents 1 and 2 disclose a sensor and a system using a quartz-crystal resonator, no study has been made on the aforementioned problems.

[Patent Document 1] Japanese Patent Application Laid-open No. Hei 11-183479
[Patent Document 2] Translated National Publication of Patent Application No. 2005-530177

SUMMARY OF THE INVENTION

The present invention has been made based on such circumstances, and an object thereof is to provide a sensing device capable of easily sensing a substance to be sensed with high accuracy.

A sensing device of the present invention being a device that uses a piezoelectric sensor structured by forming an absorption layer on an electrode provided on a piezoelectric piece and senses, by making the adsorption layer adsorb a substance to be sensed in a sample solution, the substance to be sensed based on a variation in natural frequency of the piezoelectric piece, the sensing device includes: an oscillator circuit for oscillating the piezoelectric piece; a frequency measuring part measuring an oscillation frequency of the oscillator circuit; a data obtaining part sampling a frequency measured in the frequency measuring part at a previously set time interval to obtain time-series data of the frequency; a storage part storing a previously set measuring time for measuring a variation in frequency when the sample solution is supplied to the piezoelectric sensor; and an output part sequentially calculating a frequency stability of a group of sampling spans each starting from each sampling timing of the frequency and having a length corresponding to the measuring time, for each of the sampling spans, when a reference solution which does not contain a substance to be absorbed in the absorption layer is supplied to the piezoelectric sensor and outputting a supply enable signal for the sample solution when the calculated frequency stability becomes equal to or less than a tolerance value corresponding to a measurement sensitivity.

The frequency stability is represented by the following equation, for example.

$$\text{frequency stability}$$

$$\text{frequency stability} = \frac{1}{m}\sum_{k=1}^{m}\frac{1}{2}(y_{k+1} - y_k)^2$$

$y_k$: frequency at k-th sampling time in each of sampling spans, m: number of samplings included in each of sampling spans (k, m: positive number)

The sensing device may include a tolerance value obtaining part selecting the measurement sensitivity to determine a tolerance value corresponding to the measurement sensitivity.

As a concrete structure of the present invention, it is possible to cite an example in which the sensing device includes: a sample solution supply part supplying the sample solution to the piezoelectric sensor; a reference solution supply part supplying the reference solution to the piezoelectric sensor; and a discharge part discharging the sample solution and the reference solution supplied to the piezoelectric sensor, in which the calculation of the frequency stability and the sensing of the substance to be sensed in the sample solution are performed while letting each of the reference solution and the sample solution flow into an atmosphere in which the piezoelectric sensor is put.

According to the present invention, when sensing, by using a piezoelectric sensor structured by forming an absorption layer on an electrode provided on a piezoelectric piece and making the absorption layer absorb a substance to be sensed in a sample solution, the substance to be sensed based on a variation in natural frequency of the piezoelectric piece, a reference solution is supplied before supplying a sample fluid to the absorption layer to measure an oscillation frequency of the piezoelectric piece at a previously set measurement interval, and the oscillation frequency of the piezoelectric piece is stabilized for the same period of time as the measuring time until the measurement result becomes equal to or less than a tolerance value previously set based on a measurement sensitivity of the substance to be sensed, so that the substance to be sensed can be easily sensed with high accuracy.

BRIEF DESCRIPTION OF THE DRAWINGS

FIG. 11 is a schematic view showing an example of tolerance values used for calculation performed by the aforementioned measuring part;

DETAILED DESCRIPTION OF THE PREFERRED EMBODIMENT(S)

Figure 1:
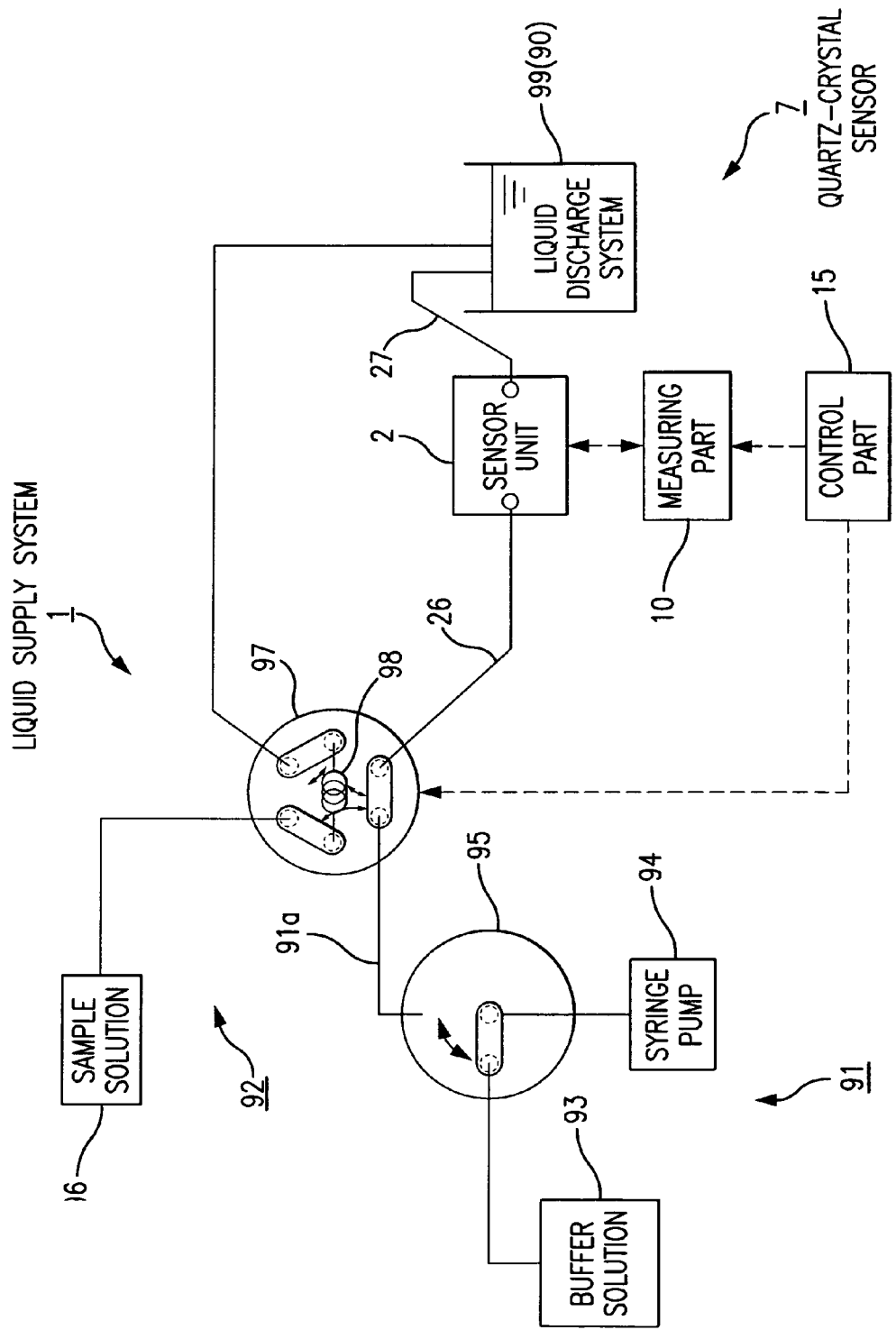
FIG. 1 is a schematic diagram showing an entire structure of a sensing device of the present invention.
Figure 2:
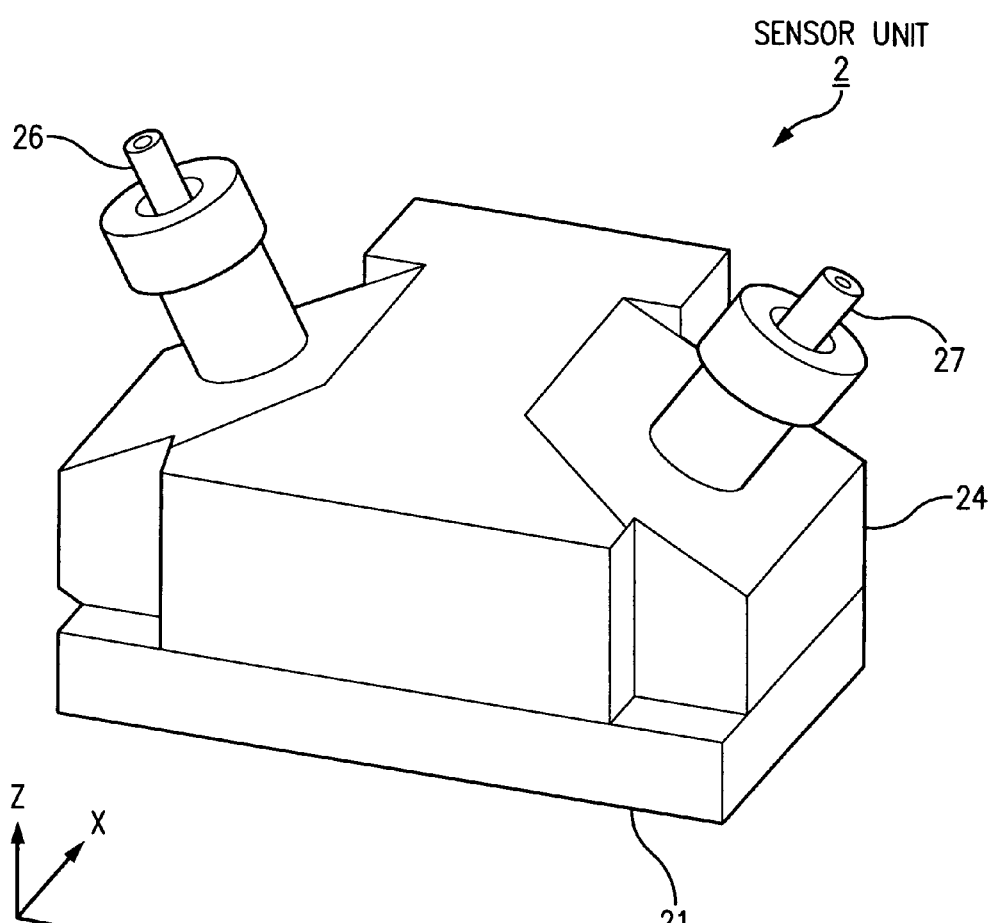
FIG. 2 is a perspective view showing an example of a sensor unit of the aforementioned sensing device.
Figure 3:
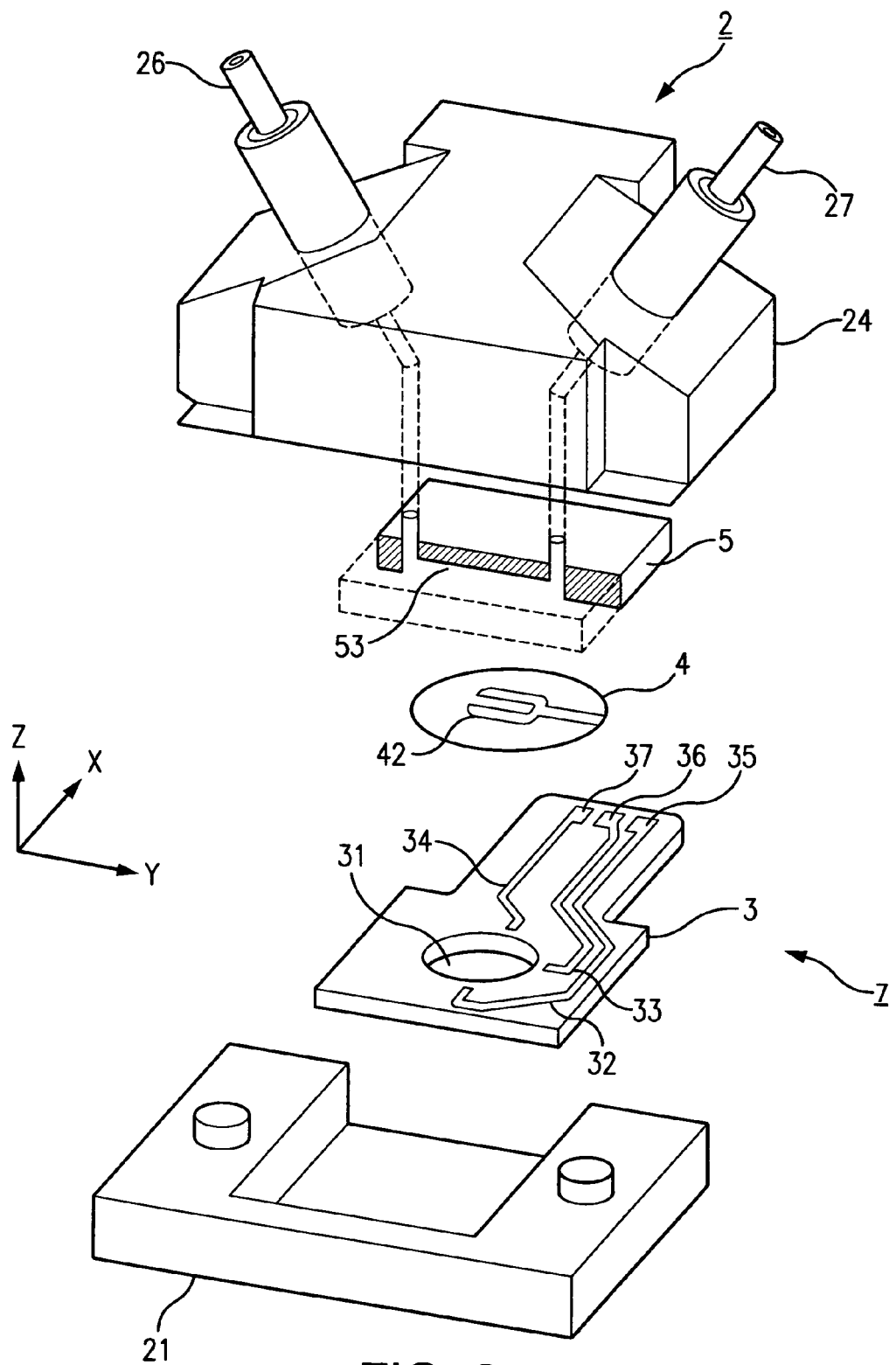
FIG. 3 is an exploded perspective view showing the aforementioned sensor unit.

As shown in FIG. 1, an embodiment of a sensing device of the present invention includes: a sensor unit 2; a liquid supply system 1 that supplies a liquid (sample solution and buffer solution) to the sensor unit 2; a liquid discharge system 90 that stores the liquid discharged from the sensor unit 2; and a frequency measuring part 10 that drives a quartz-crystal sensor 7 being a piezoelectric sensor mounted to the sensor unit 2 and processes an obtained oscillation output. As shown in FIG. 2 and FIG. 3, the sensor unit 2 is formed of a support 21, a sealing member 30, (not shown), a wiring board 3, a quartz-crystal resonator 4, a channel forming member 5 and an upper cover 24, which are stacked in this order from the bottom.

Figure 4A:
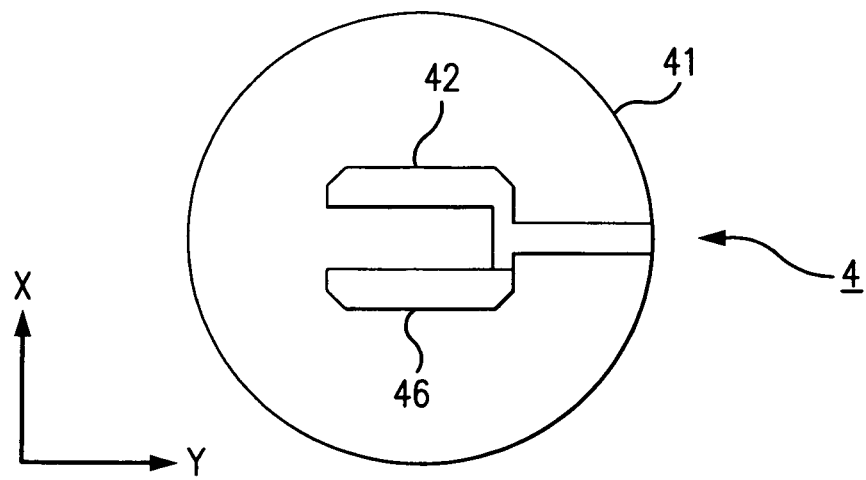
FIGS. 4(a) and 4(b) are plan views showing an example of a quartz-crystal resonator used in the aforementioned sensor unit.
Figure 4B:
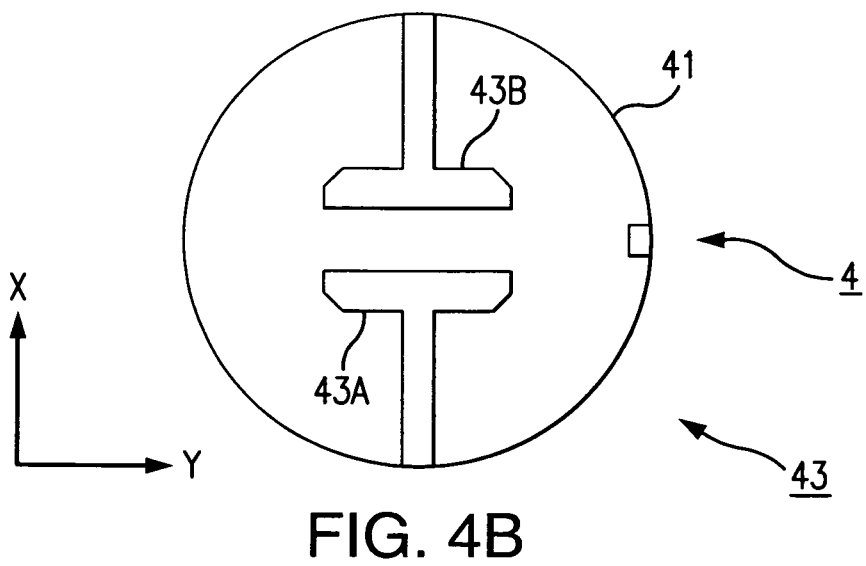
Figure 5:
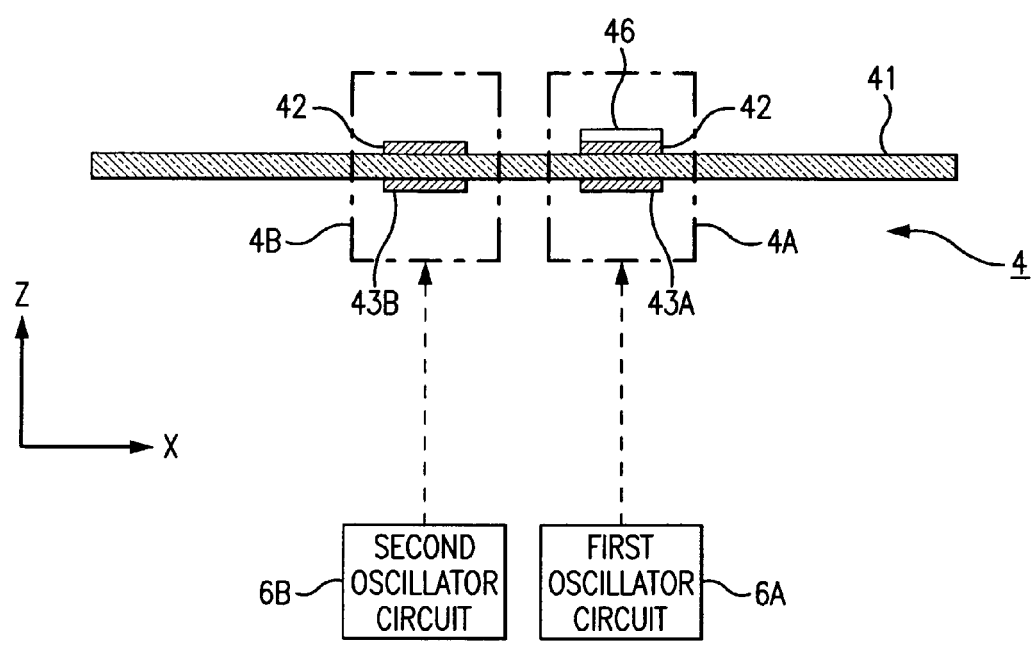
FIG. 5 is a longitudinal sectional view showing the aforementioned quartz-crystal resonator.

The quartz-crystal sensor 7 is formed by providing the quartz-crystal resonator 4 being a piezoelectric resonator on the wiring board 3. As shown in FIGS. 4a and 4b for instance, the quartz-crystal resonator 4 is formed by providing excitation electrodes 42, 43 on both surfaces of a quartz-crystal piece 41 in a disk shape being a piezoelectric piece and, in this example, a first excitation electrode 43A and a second excitation electrode 43B are disposed to be separated from each other on a rear surface side and an excitation electrode (common electrode) 42 common to the aforementioned two excitation electrodes 43A, 43B is disposed on a front surface side of the quartz-crystal piece 41. Accordingly, as shown in FIG. 5, the first excitation electrode 43A and the common electrode 42 form a first oscillation area 4A, and the second excitation electrode 43B and the common electrode 42 form a second oscillation area 4B. When the quartz-crystal sensor 7 is mounted to the sensor unit 2, the first excitation electrode 43A and the second excitation electrode 43B are respectively connected to later-described two oscillator circuits 6A, 6B provided in the measuring part 10 via conductive paths 32, 34 on the wiring board 3, and the common electrode 42 is connected to a ground side of the oscillator circuits 6A, 6B via a conductive path 33 on the wiring board 3. On an end area of the aforementioned wiring board 3, connection terminals 35, 36, and 37 respectively connected to the respective conductive paths 32, 33, and 34 are formed.

Figure 6:
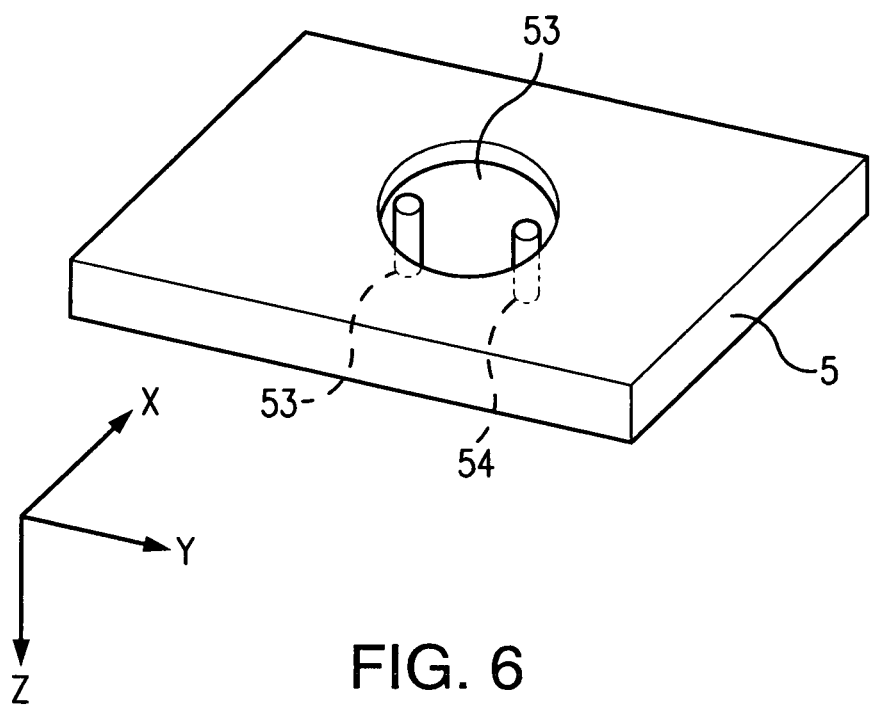
FIG. 6 is a perspective view showing a channel forming member used in the aforementioned sensor unit.
Figure 7:
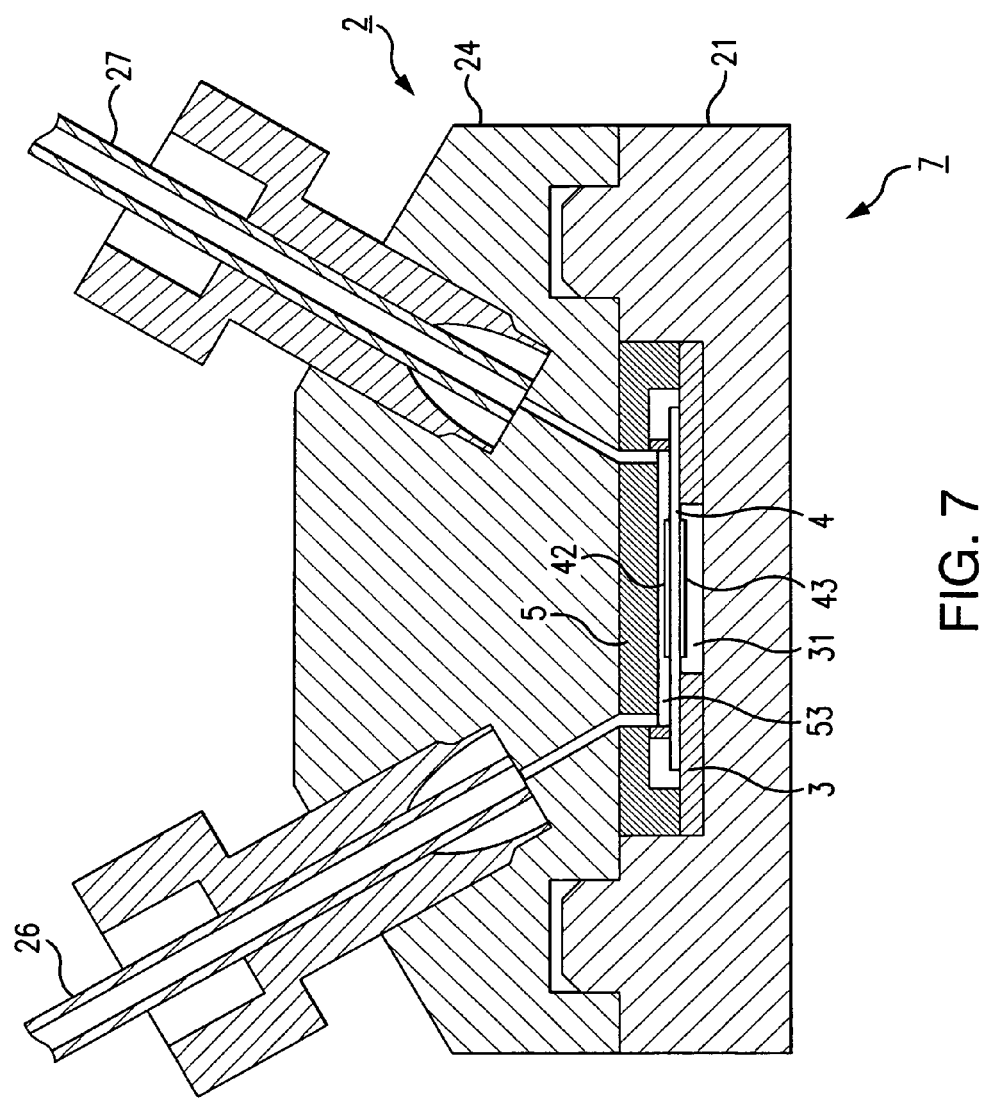
FIG. 7 is a longitudinal sectional view showing the aforementioned sensor unit.

As shown in FIG. 3 and FIG. 7, the quartz-crystal resonator 4 is mounted to block a through hole 31 formed on the wiring board 3, and the quartz-crystal sensor 7 is mounted to the sensor unit 2 in a state where a front surface side and a rear surface side thereof are respectively pressed by the channel forming member 5 formed of an elastic member shown in FIG. 6 and the support 21, as shown in FIG. 7.

Further, on an area corresponding to the first excitation electrode 43A of the common electrode 42 of the quartz-crystal sensor 7, an absorption layer (reactant) 46 formed of an antibody for absorbing an antigen, for instance, being a substance to be sensed is formed, as shown in FIG. 5. Therefore, when a substance to be sensed in a sample solution, for instance, is absorbed in the aforementioned absorption layer 46, an oscillation frequency in the first oscillation area 4A is lowered by a mass load effect, and meanwhile, the substance to be sensed is not absorbed in the common electrode 42 in the second oscillation area 4B. Accordingly, by comparing the oscillation frequencies in the respective areas 4A, 4B before and after the absorption of the substance to be sensed, it becomes possible to sense a variation (amount of decrease) in the oscillation frequency corresponding to an amount of the substance to be sensed absorbed in the absorption layer 46, by reducing an influence of disturbance such as a temperature surrounding the sensor unit 2, a viscosity of the sample solution, and an adhesion of a substance other than the substance to be sensed contained in the sample solution.

In FIG. 2, FIG. 3 and FIG. 7, reference numeral 26 denotes a liquid supply pipe and reference numeral 27 denotes a liquid discharge pipe being a discharge unit, in which it is structured such that a liquid supplied from the liquid supply pipe 26 passes through a liquid supply area 53 as a channel between the channel forming member 5 and the quartz-crystal resonator 4 and is discharged from the liquid discharge pipe 27. Further, as shown in FIG. 1, the liquid supply system 1 is formed of a buffer solution supply part 91 and a sample solution supply part 92 which supply the buffer solution as the reference solution and the sample solution, respectively, to the quartz-crystal sensor 7. The buffer solution supply part 91 includes a buffer solution reservoir part 93 that stores a buffer solution which is, for instance, a phosphoric acid buffer, a buffer solution holding part 94 such as, for example, a syringe pump, and a first valve 95 formed of, for instance, a three-way valve or the like, in which it is structured such that the buffer solution is once sucked to be held from the buffer solution reservoir part 93 by the buffer solution holding part 94, and then a channel of the first valve 95 is switched so that the buffer solution can be supplied to the quartz-crystal sensor 7 from the buffer solution holding part 94, as shown in FIG. 8(*a*).

Figure 8A:
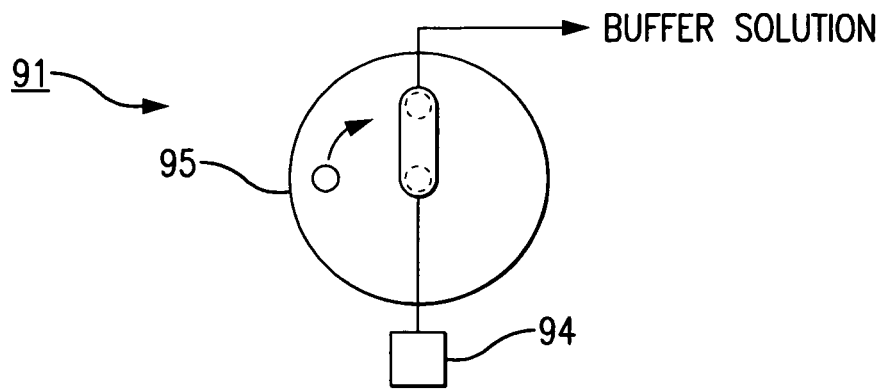
FIGS. 8(a), 8(b) and 8(c) are schematic views showing states where a buffer solution and a sample solution are supplied to the aforementioned sensor unit.
Figure 8B:
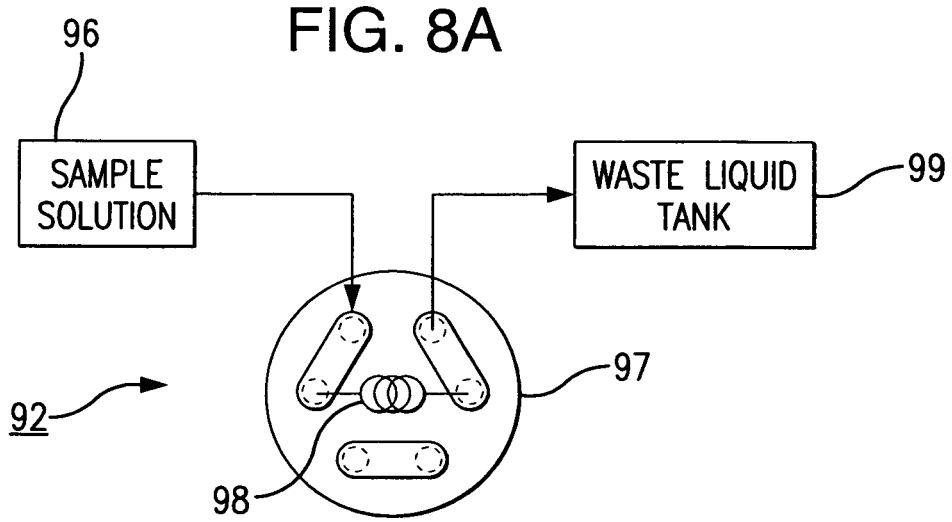
Figure 8C:
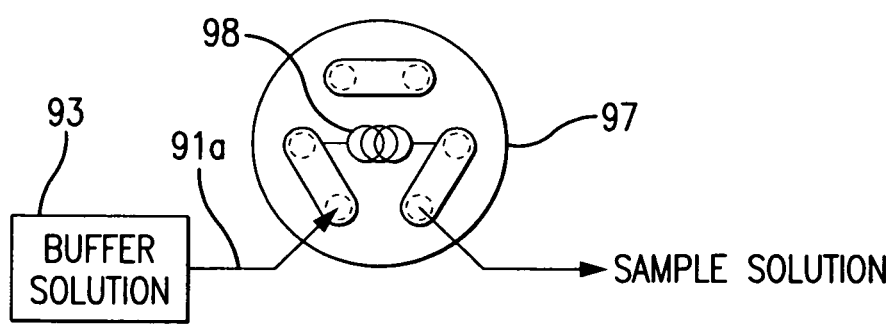

The sample solution supply part 92 includes a sample solution reservoir part 96 that stores a sample solution which is, for example, blood or serum, and a second valve 97 formed of, for instance, a six-way valve or the like, in which it is structured such that the sample solution in the sample solution reservoir part 96 is filled in a column 98 provided in the second valve 97, as shown in FIG. 8(*b*), and then a channel of the second valve 97 is switched so that the sample solution in the column 98 is pushed out by the buffer solution and supplied to the quartz-crystal sensor 7, as shown in FIG. 8(*c*). In FIG. 1, reference numerals 91*a* and 99 respectively denote a buffer solution supply channel extending toward the quartz-crystal sensor 7 from the first valve 95 via the second valve 97, and a liquid discharge part forming the liquid discharge system 90, in which it is structured such that when the buffer solution is supplied to the quartz-crystal sensor 7, the buffer solution flows through the second valve 97 without passing through the column 98, and an excess sample solution overflowed from the column 98 is discharged to the liquid discharge part 99.

Figure 9:
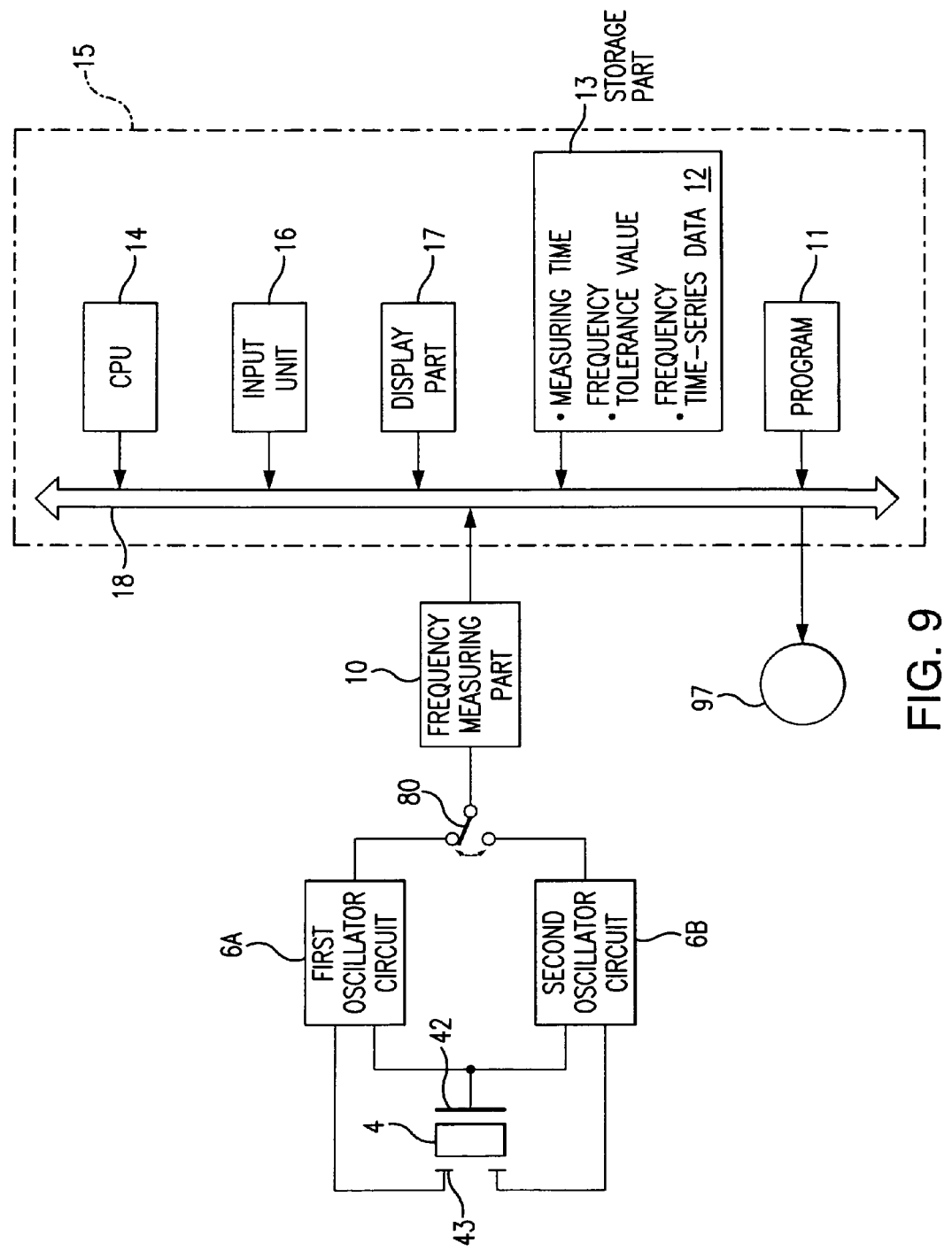
FIG. 9 is a schematic diagram showing a measuring part 10 in the sensing device.

Next, the measuring part 10 will be described with reference to FIG. 9. In FIG. 9, reference numeral 6A denotes a first oscillator circuit for oscillating the first is oscillation area 4A of the quartz-crystal resonator 4, and reference numeral 6B denotes a second oscillator circuit for oscillating the second oscillation area 4B of the quartz-crystal resonator 4, in which oscillation outputs (frequency signals) of these oscillator circuits are structured to be alternately taken into the measuring part 10 with the use of a switch part 80. The measuring part 10 may be one that detects the frequencies by a frequency counter, which is a publicly known circuit, but may be one that uses a method of A/D-converting the frequency signals, processing the resultants by a carrier move, generating rotation vectors rotating at the frequencies of the frequency signals, and finding the velocities of the rotation vectors, as described in, for example, Japanese Patent Application Laid-open No. 2006-258787. The use of the measuring part that performs such digital processing enables frequency detection with higher accuracy and therefore is more preferable.

Thus obtained frequency signal is sampled at every one sec, for instance by a program (although being stored in a program storage part, it is illustrated as a program) 11, and stored in a storage part 13 as time-series data 12. Here, reference numerals 15 and 18 in FIG. 9 respectively denote a control part formed of a computer and a bus, and the control part includes the aforementioned program 11, the storage part 13, a CPU 14, an input unit 16 with which, for instance, an operator inputs later-described measuring time, frequency tolerance values and the like, a display part 17 on which the result of measurement of the frequency and the substance to be sensed is displayed, and so on. The storage part 13 stores the measuring time and the frequency tolerance values.

Figure 10:
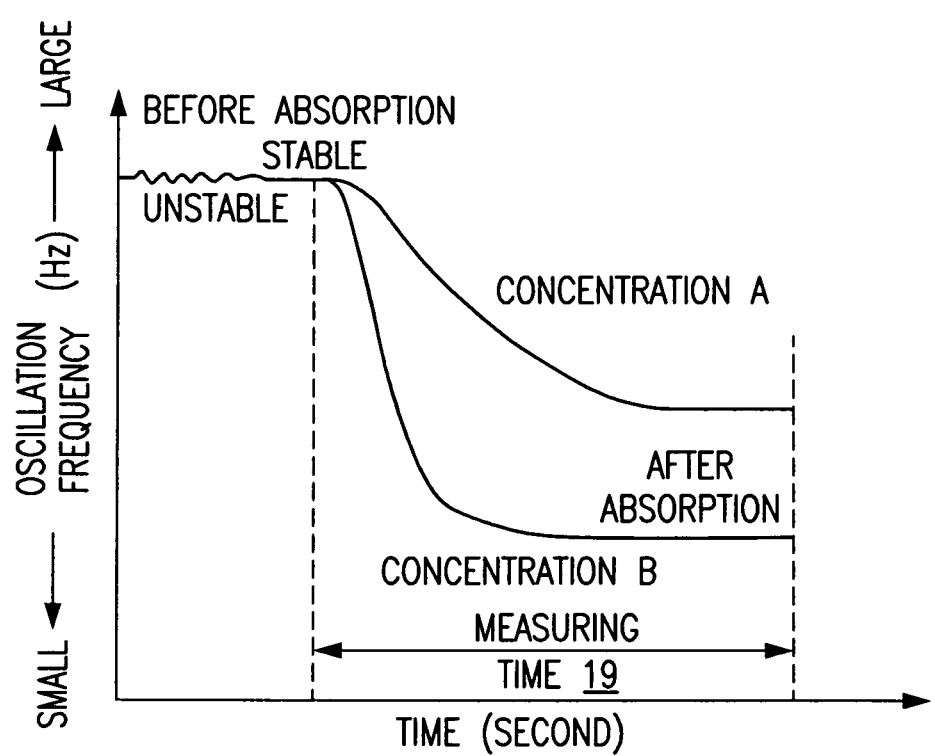
FIG. 10 is a characteristic diagram showing a characteristic obtained when a sample fluid is sensed in the aforementioned sensing device.

The measuring time is a period of time required for obtaining, when the sample solution is supplied to the quartz-crystal sensor 7, a variation (amount of decrease) in the frequency caused by the absorption of the substance to be sensed in the sample solution in the quartz-crystal sensor 7. Although the period of time until the frequency is lowered and stabilized when the sample solution is supplied to the quartz-crystal sensor 7 varies depending on a concentration of the substance to be sensed as shown in FIG. 10, in this device, the measuring time corresponds to a period of time (five minutes, for example) during which the sample solution in the column 98 passes through the quartz-crystal sensor 7, for instance. Further, for example, a frequency of the first oscillation area 4A at a predetermined time point after the measuring time elapses or a frequency of the first oscillation area 4A when a gradient of decreasing curve of frequency becomes smaller than a predetermined value, is uniformly evaluated as a frequency when the substance to be sensed with an amount corresponding to the concentration of the substance to be sensed in the sample solution is absorbed in the quartz-crystal sensor 7 (absorption layer 46). Further, when a calibration curve indicating a correspondence between a concentration of a substance to be sensed in a sample solution and an amount of decrease in frequency is formed, namely, when a substance to be sensed is sensed in a sample solution of known concentration to measure an amount of decrease in frequency corresponding to a concentration of the substance to be sensed, if a stabilization time required for lowering and stabilizing the frequency is previously known to be shorter than the passing time of the sample solution when the solution passes through the column 98, and the sampling is completed at a time point when the stabilization time elapses and a frequency at this time is used as a frequency after the absorption of the substance to be sensed, the stabilization time corresponds to the measuring time.

Further, the frequency tolerance value is a threshold value for determining, when the frequency is judged to be stabilized or not, whether or not a value ($\sigma^2(\tau)$) to be an index of the stabilization of frequency as will be described later becomes a sufficiently small value which indicates the stabilization. The frequency tolerance value changes depending on a set measurement sensitivity (resolution), as shown in FIG. 11, for instance, and in a case where an oscillation frequency of the quartz-crystal resonator 4 is 30 MHz, for example, a noise (error range 19*b*) acceptable during a measuring time when a measurement sensitivity is 5 Hz, for instance, is set to 0.5 Hz (0.0167 ppm when a 30-MHz quartz-crystal sensor is employed), for example, and a tolerance value of $\sigma^2(t)$ corresponding to the error range becomes equal to or less than $1.67 \times 10^{-8}$ (0.0167 ppm). Here, it is also possible to design such that a table of frequency tolerance values corresponding to the measurement sensitivities as shown in FIG. 11 is previously stored in the storage part 13, and the program 11 obtains the frequency tolerance value from the table based on the measurement sensitivity input or selected by the operator. Alternatively, it is also possible to design such that a ratio of noise with respect to the measurement sensitivity (0.1, in this example) is previously stored in the storage part, and when the measurement sensitivity is selected, the measurement sensitivity is multiplied by the ratio of noise to determine an acceptable noise (error range).

The program 11 includes, in addition to a step group for performing the sampling of the time-series data 12, a step group for performing a switching sequence of the respective valves 95, 97, and a step group for determining the aforementioned amount of decrease in frequency when the sample solution is supplied to the quartz-crystal sensor 7 based on the time-series data 12. Further, the program 11 includes a step group for judging the stabilization of frequency when the buffer solution is supplied to the quartz-crystal sensor 7. The judgment of stabilization of frequency will be described hereinbelow, in which whether the oscillation frequency of the quartz-crystal resonator 4 is stabilized or not is calculated based on the Allan Deviation equation represented by the following equation (1), for instance.

$$\sigma_y^2(\tau) = \sigma_y^2(\tau, m) = \frac{1}{m}\sum_{k=1}^{m}\frac{1}{2}(y_{k+1} - y_k)^2 \quad (1)$$

$y_k$: frequency at k-th sampling time in each of sampling spans, m: number of samplings included in each of sampling spans (k, m: positive number)

Figure 12:
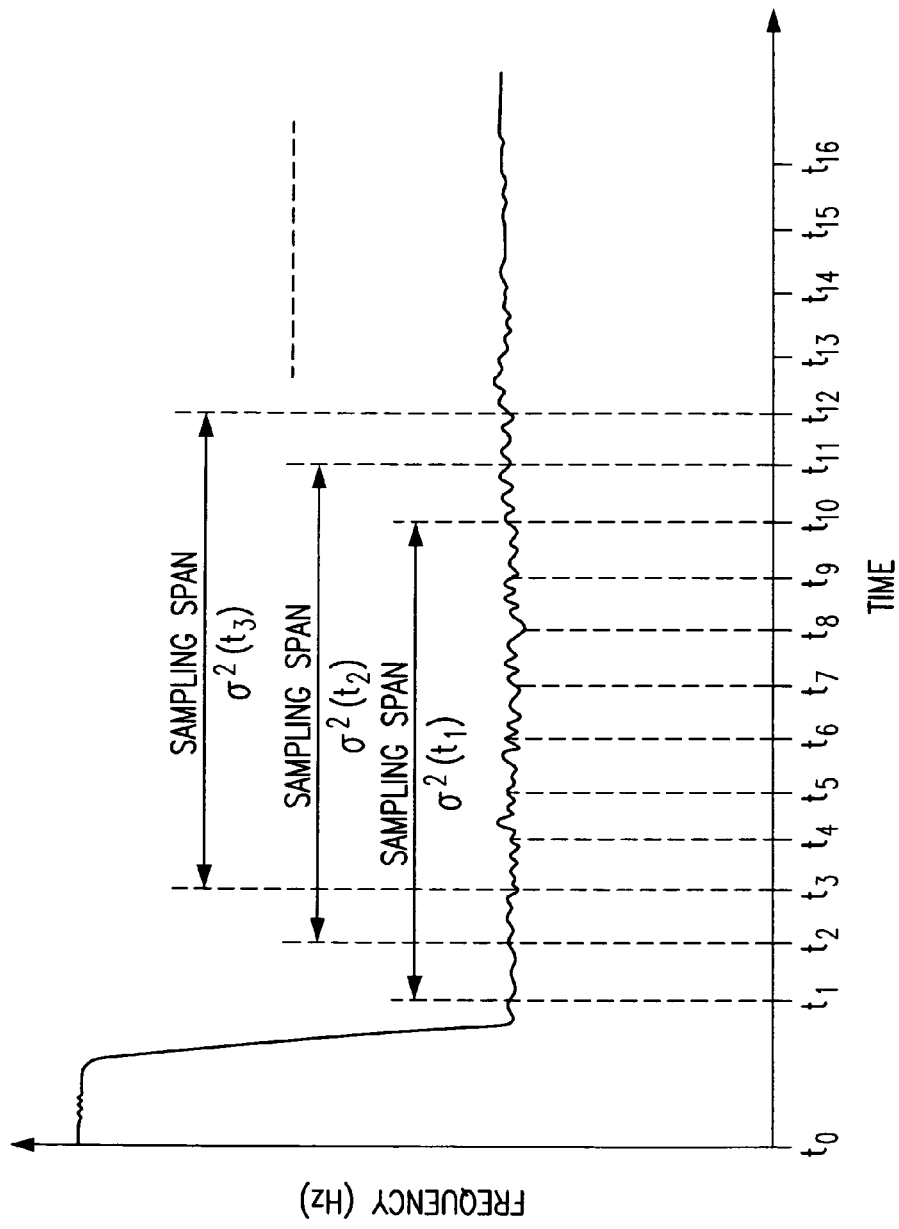
FIG. 12 is a schematic view showing frequency data obtained by the measuring part.
Figure 13:
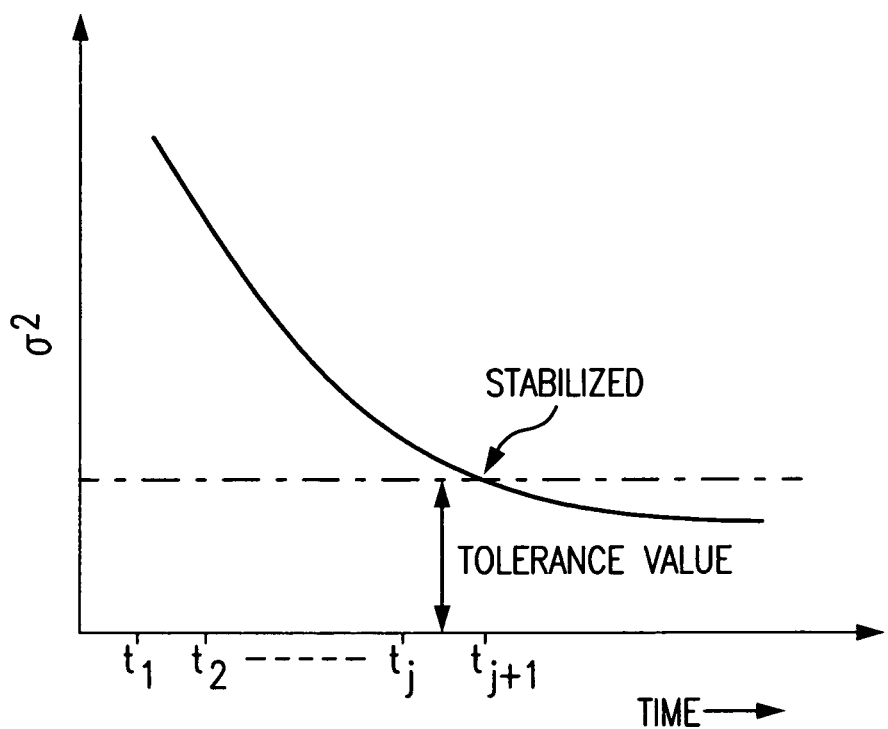
FIG. 13 is a schematic view showing an example of calculation method performed in a control part of the aforementioned sensing device.

In the equation (1), $y_k$ is a frequency at k-th sampling time in each of sampling spans and m is the number of samplings included in each of sampling spans (k, m: positive number), and in this example, a difference in oscillation frequencies $(y_{k+1}-y_k)$ is calculated at every one second, for instance, after the buffer solution is supplied to the quartz-crystal sensor 7 and the sampling is started, and a measured result $\sigma^2$ being a result obtained by adding a square value of the difference in oscillation frequencies until a measuring time 19 elapses (until m-number of frequencies are obtained) and dividing the resultant by 2 m, is calculated. Further, as shown in FIG. 12, the measured result $\sigma^2$ is updated at every one second after the measuring time 19 elapses after the sampling is started, namely, a start point of sampling is newly set at every one second, and $\sigma^2(t_1)$, $\sigma^2(t_2)$, $\sigma^2(t_3)$, . . . , $\sigma^2(t_j)$, $\sigma^2(t_{j+1})$, . . . are sequentially obtained for the respective sampling spans. As above, as shown in FIG. 13, the aforementioned measured result $\sigma^2$ is reduced to a predetermined value as the oscillation frequency is stabilized with the elapse of time after the sampling is started, and when the measured result $\sigma^2$ (specifically, standard deviation $\sigma$, as will be described hereinafter) becomes smaller than the aforementioned frequency tolerance value, the aforementioned program 11 judges that the frequency is stabilized, and outputs the supply enable signal for the sample solution to start the supply of the sample solution by switching the aforementioned second valve 97 from the buffer solution side to the sample solution side. In this example, a part of the step group in the program 11 corresponds to an output part that outputs the supply enable signal for the sample solution.

Here, in the above-described equation (1), since $\sigma$ becomes a mean value indicating an error, if a tolerance value of noise (error) when the measurement sensitivity is 5 Hz as above, for instance, is defined as 0.5 Hz, to be the variance can be broadly interpreted as $\sigma \approx 0.5$. Specifically, since the standard deviation ($\sigma$) is used in the aforementioned equation (1), the standard deviation is treated as the tolerance value in the measurement sensitivity. The judgment of stabilization of frequency as above is performed on, for instance, the oscillation frequency of the first oscillation area 4A or the oscillation frequency of both the first oscillation area 4A and the second oscillation area 4B. Note that FIG. 12 schematically illustrates the sampling span as nine seconds, and indicates a time point at which the oscillation of the quartz-crystal resonator 4 is started before the buffer solution is supplied, as t0.

Figure 14:
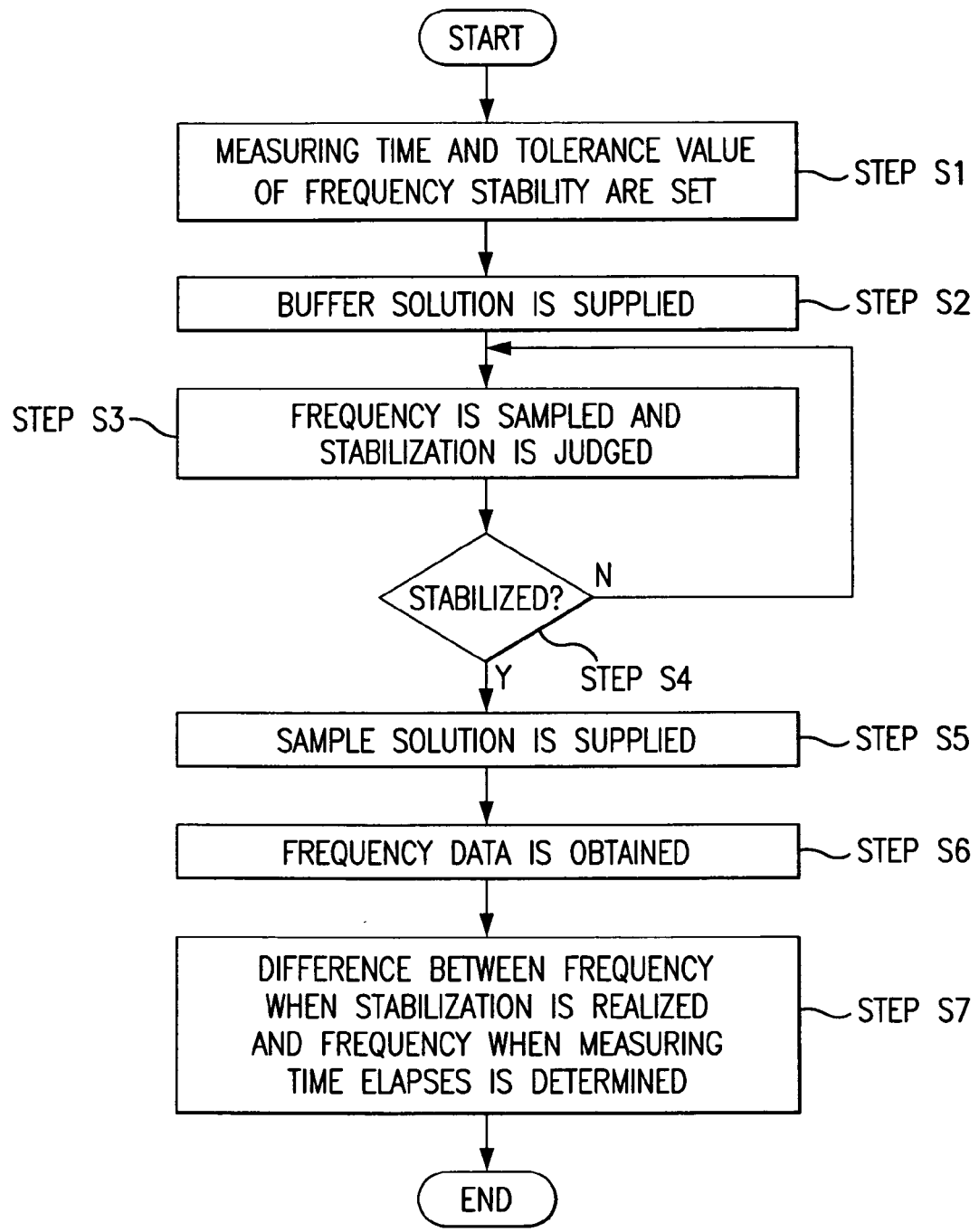
FIG. 14 is a schematic diagram showing a flow when a substance to be sensed is sensed in the aforementioned sensing device.

Next, the operation of the sensing device will be described with reference to FIG. 14. First, the quartz-crystal resonator 4 is housed in the sensor unit 2 to be airtightly integrated with the sensor unit 2 as shown in FIG. 2, and the oscillation areas 4A, 4B and the oscillator circuits 6A, 6B are electrically connected respectively via the connection terminals 35, 36, and 37 formed on the wiring board 3. Further, for instance, an operator inputs (selects) the measuring time (amount of sample solution stored in the column 98), and the frequency tolerance value or the measurement sensitivity in accordance with the sample solution to be measured (step S1). When the measurement sensitivity is input, a ratio of noise with respect to the measurement sensitivity (0.1, in the above example) is previously stored in the storage part, and the measurement sensitivity is multiplied by the ratio to determine the tolerance value.

Subsequently, the oscillation of the quartz-crystal resonator 4 (oscillation areas 4A, 4B) is started at a predetermined frequency of, for example, 30 MHz by the oscillator circuits 6A, 6B respectively, and at the same time, the buffer solution is supplied to the liquid supply area 53 from the buffer solution supply part 91 via the valves 95, 97 (step S2). Each oscillation frequency of the respective oscillation areas 4A, 4B is sampled by the measuring part 10, and the frequency is decreased to a predetermined value when the buffer solution is supplied. The oscillation frequency of the quartz-crystal resonator 4 at this time varies up and down as shown in FIG. 10 since an oscillation state is unstable right after the start of oscillation, and thereafter, the frequency is stabilized with the elapse of time. Further, as is shown in the aforementioned FIG. 13, the frequency stabilizing program 11 judges, during the same period of time as the measuring time for measuring the substance to be sensed, whether or not the standard deviation $\sigma$ is stabilized to be equal to or less than the aforementioned frequency tolerance value (step S3), and the measurement of the substance to be sensed is not performed until the oscillation frequency of the quartz-crystal resonator 4 is stabilized, namely, the waiting time is provided. Subsequently, when it is judged that the frequency is stabilized (step S4), the sensing of the substance to be sensed is started in a manner as will be described below.

Figure 15A:
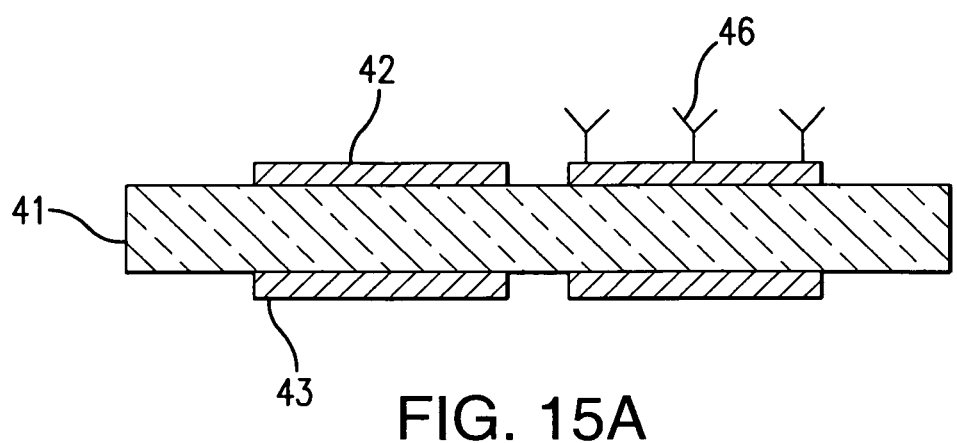
FIGS. 15(a) and 15(b) are schematic diagrams showing states where the substance to be sensed is sensed in the aforementioned sensing device.
Figure 15B:
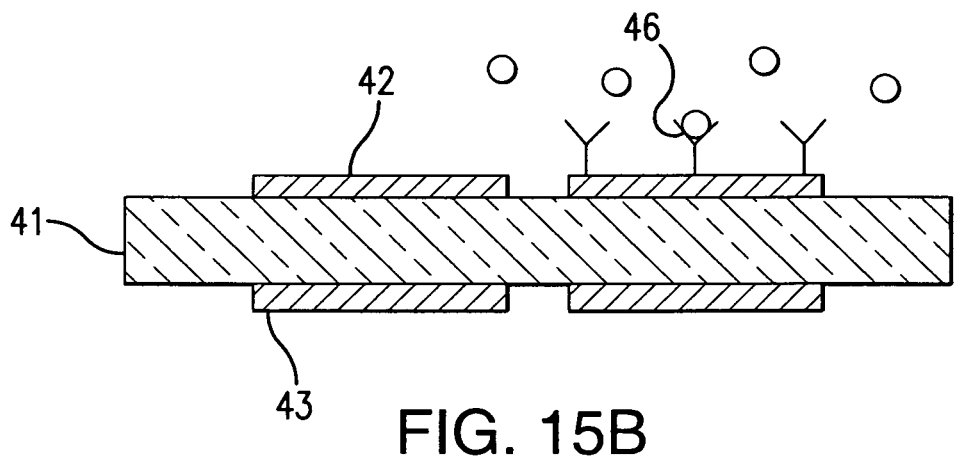

Subsequently, the sample solution is previously supplied to the column 98 of the second valve 97, and by switching the channel of the second valve 97 while oscillating the quartz-crystal resonator 4, the buffer solution is supplied to the column 98 from the buffer solution supply part 91 (step S5). The sample solution in the column 98 is pushed out by the buffer solution to be supplied to the liquid supply area 53. Further, when the substance to be sensed is brought into contact with the absorption layer 46 of the quartz-crystal resonator 4 shown in FIG. 15(*a*), the substance to be sensed is absorbed in the absorption layer 46 through, for example, an antigen-antibody reaction, a chemical reaction and the like, as shown in FIG. 15(*b*), the oscillation frequency of the quartz-crystal resonator 4 (oscillation area 4A) is decreased due to a mass load effect, and frequency data at this time is obtained (step S6). After that, by supplying the sample solution to the liquid supply area 53 for a period of time equal to the measuring time, the substance to be sensed with an amount corresponding to the concentration of the substance to be sensed in the sample solution is absorbed in the absorption layer 46 and the oscillation frequency of the quartz-crystal resonator 4 (oscillation area 4A) is decreased to a predetermined value, as shown in the aforementioned FIG. 10. The frequency data obtained at this time is measured at, for instance, a previously set measurement sensitivity, namely, in a unit of 5 Hz, for instance, and the error range (noise) during the measuring time is reduced to 0.5 Hz or less. Thereafter, when the measuring time elapses, the solution supplied to the liquid supply area 53 is switched from the sample solution to the buffer solution. Note that in this example, a difference between a frequency right before the sample solution in the column is supplied to the quartz-crystal resonator 4 (frequency when the buffer solution is supplied) and a frequency right after the sample solution passes through the quartz-crystal resonator 4 and is switched to the buffer solution pushing out the sample solution, is determined. Accordingly, the measuring time corresponds to a period of time from when the sample solution just about reaches the quartz-crystal resonator 4 to when the sample solution just passes through the resonator.

Thereafter, in step S7, a difference between a frequency at a time point when the buffer solution is supplied to the quartz-crystal sensor 7 and the frequency is judged to be stabilized, and a frequency at a time at which a predetermined period of time elapses after the measuring time elapses or a frequency at a time at which a gradient of decreasing curve of frequency takes a predetermined value, is determined. Specifically, a difference in frequencies in the first oscillation area 4A (detection area) of the quartz-crystal resonator 4 and a difference in frequencies in the second oscillation area 4B (reference area) of the quartz-crystal resonator 4 are determined. Since the difference in frequencies in the second oscillation area 4B is generated due to a disturbance such as a temperature change and a viscosity of the sample solution, or an adhesion of a substance other than the substance to be sensed contained in the sample solution, as described above, by subtracting the difference in the second oscillation area 4B from the difference in the first oscillation area 4A, it is possible to obtain a difference in frequency caused only by the absorption of the substance to be sensed, in which the variance in frequency due to the disturbance is compensated. A value of the difference is used for forming the aforementioned calibration curve, or is evaluated, by being compared with a previously formed calibration curve, as a concentration or a presence/absence of the substance to be sensed in the sample solution, for instance.

According to the aforementioned embodiment, when sensing, by supplying the sample solution to the absorption layer 46 while oscillating the quartz-crystal resonator 4 to make the absorption layer absorb the substance to be sensed in the sample solution, the substance to be sensed based on an amount of variation in the oscillation frequency of the quartz-crystal resonator 4, the buffer solution is supplied before supplying the sample solution to the absorption layer 46 to measure the oscillation frequency of the quartz-crystal resonator 4 at a predetermined measurement interval, for instance, at every one second, and the oscillation frequency of the quartz-crystal resonator 4 is stabilized for the same period of time as the measuring time until the measurement result $\sigma^2(t)$ becomes equal to or less than the frequency tolerance value previously set based on the measurement sensitivity of the substance to be sensed, so that the substance to be sensed can be easily sensed with high accuracy.

Further, since the Allan Deviation equation is used for judging the stabilization of oscillation frequency as described above, the stabilization of frequency can be judged easily and securely.

Further, when sensing the substance to be sensed, by measuring the oscillation frequency while supplying the sample solution, the amount of decrease in frequency corresponding to the concentration of the substance to be sensed can be accurately calculated, which enables to accurately sense the substance to be sensed, and since an influence of a temperature surrounding the sensor unit 2 and the like is reduced by providing the two oscillation areas 4A, 4B on the one quartz-crystal resonator 4 in which one oscillation area 4A is set as an area for measurement and the other oscillation area 4B is set as an area for reference, the substance to be sensed can be sensed with high accuracy.

In the above example, the two oscillation areas 4A, 4B are provided to reduce the influence of the temperature surrounding the sensor unit 2 and the like, but, it is also possible to provide only one oscillation area. Further, although the oscillation frequency is measured while supplying the buffer solution and the sample solution, the measurement may also be conducted in a sort of closed system by dropping the buffer solution and the sample solution onto the excitation electrodes 43A, 43B.

In the above description, the buffer solution is an example of the reference solution. The reference solution has to be a liquid that does not contain a substance to be absorbed in the absorption layer of the piezoelectric sensor and, for instance, pure water or the like can also be used as the reference solution. Although the reference solution is preferably a buffer solution when blood or serum is used as the sample solution, it is preferable to use pure water as the reference solution when a pollutant in an environmental water such as river is detected as a substance to be sensed.

Further, although the presence/absence or the concentration of the substance to be sensed is calculated by the measuring part 10 as described above, it is also possible that, for example, the oscillation frequencies obtained in the respective oscillation areas 4A, 4B are displayed on the display part 17, the operator reads the display on the display part 17 and compares the read result and the aforementioned calibration curve or threshold value to determine the presence/absence or the concentration of the substance to be sensed. Further, although the buffer solution is switched to the sample solution by the measuring part 10 (control part 15) after the frequency is stabilized, it is also possible that, for example, the display part 17 displays whether or not the frequency is stabilized, and the operator switches the second valve 97 based on the display.

Further, when the sample solution being a liquid is used, the buffer solution being a liquid is supplied to the liquid supply area 53 when stabilizing the oscillation frequency of the quartz-crystal resonator 4, but, it is also possible to use the sensor unit 2 for sensing a substance to be sensed in a gas, for example, for sensing dioxin, alcohol or the like in a gas. In such a case, a clean gas, for instance, instead of the buffer solution is used when stabilizing the oscillation frequency of the quartz-crystal resonator 4.

What is claimed is:

1. A sensing device that uses a piezoelectric sensor structured by forming an absorption layer on an electrode provided on a piezoelectric piece and senses, by making the adsorption layer adsorb a substance to be sensed in a sample solution, the substance to be sensed based on a variation in natural frequency of the piezoelectric piece, the sensing device comprising:

an oscillator circuit for oscillating the piezoelectric piece;
a frequency measuring part measuring an oscillation frequency of said oscillator circuit;
a data obtaining part sampling a frequency measured in said frequency measuring part at a previously set time interval to obtain time-series data of the frequency;
a storage part storing a previously set measuring time for measuring a variation in frequency when the sample solution is supplied to the piezoelectric sensor; and
an output part sequentially calculating a frequency stability of a group of sampling spans each starting from each sampling timing of the frequency and having a length corresponding to the measuring time, for each of the sampling spans, when a reference solution which does not contain a substance to be absorbed in the absorption layer is supplied to the piezoelectric sensor and outputting a supply enable signal for the sample solution when the calculated frequency stability becomes equal to or less than a tolerance value corresponding to a measurement sensitivity.

2. The sensing device according to claim 1, wherein the frequency stability is represented by the following equation.

$$\text{frequency stability} = \frac{1}{m}\sum_{k=1}^{m}\frac{1}{2}(y_{k+1} - y_k)^2$$

$y_k$: frequency at k-th sampling time in each of sampling spans, m: number of samplings included in each of sampling spans (k, m: positive number)

3. The sensing device according to claim 1, further comprising a tolerance value obtaining part selecting the measurement sensitivity to determine the tolerance value corresponding to the measurement sensitivity.

4. The sensing device according to claim 1, further comprising:
a sample solution supply part supplying the sample solution to the piezoelectric sensor; a reference solution supply part supplying the reference solution to the piezoelectric sensor; and
a discharge part discharging the sample solution and the reference solution supplied to the piezoelectric sensor, wherein the calculation of the frequency stability and the sensing of the substance to be sensed in the sample solution are performed while letting each of the reference solution and the sample solution flow into an atmosphere in which the piezoelectric sensor is put.

5. The sensing device according to claim 4, further comprising a liquid switching part switching the supply of liquid to the piezoelectric sensor from the reference solution to the sample solution, based on the output of the supply enable signal.

* * * * *